United States Patent
Dickinson et al.

[11] Patent Number: 6,006,613
[45] Date of Patent: Dec. 28, 1999

[54] UNDERWATER SAMPLING APPARATUS

[75] Inventors: Michael L. Dickinson, Saginaw; Stacy K. Hilaski, Stanford; Linda K. Jackson; William H. Phillips, both of Saginaw, all of Mich.

[73] Assignee: Trippensee Corporation, Saginaw, Mich.

[21] Appl. No.: 08/890,046

[22] Filed: Jul. 9, 1997

[51] Int. Cl.⁶ ............................................. G01N 1/14
[52] U.S. Cl. ............................. 73/864.66; 73/864.67
[58] Field of Search ......................... 73/864.63, 864.66, 73/864.67

[56] References Cited

U.S. PATENT DOCUMENTS

| | | | |
|---|---|---|---|
| 3,949,497 | 4/1976 | Crump | 73/864.42 X |
| 5,460,056 | 10/1995 | Phillips | 73/864.66 |
| 5,487,314 | 1/1996 | Phillips | 73/864.66 |
| 5,821,437 | 10/1998 | Budin | 73/864.67 X |

FOREIGN PATENT DOCUMENTS

| | | | |
|---|---|---|---|
| 174036 | 8/1965 | U.S.S.R. | 73/864.66 |
| 527628 | 9/1976 | U.S.S.R. | 73/864.66 |
| 562747 | 6/1977 | U.S.S.R. | 73/864.66 |
| 744267 | 6/1980 | U.S.S.R. | 73/864.66 |
| 893876 | 12/1981 | U.S.S.R. | 73/864.66 |
| 1326941 | 7/1987 | U.S.S.R. | 73/864.66 |

*Primary Examiner*—Thomas P. Noland
*Attorney, Agent, or Firm*—Reising, Ethington, Barnes, Kisselle, Learman & McCulloch P.C.

[57] ABSTRACT

An underwater sampler has a tubular body having closures biased to move from open to closed positions. The closures releasably may be latched in their open position by a latch mechanism having retainers separably coupled to anchor cables attached to the respective closures. The latch mechanism may be actuated by a weighted messenger or by a sharp tug on a hoist line by which the tubular body is suspended at a predetermined level in a body of water from which a sample is to be taken.

20 Claims, 4 Drawing Sheets

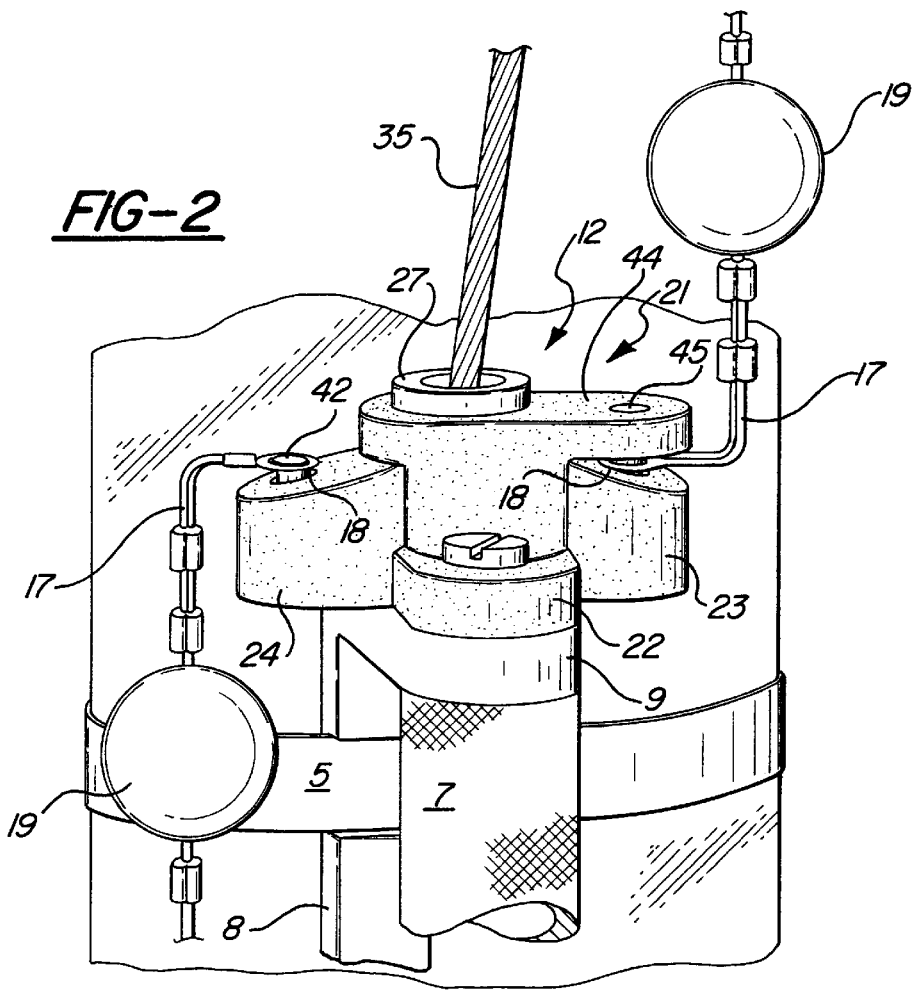
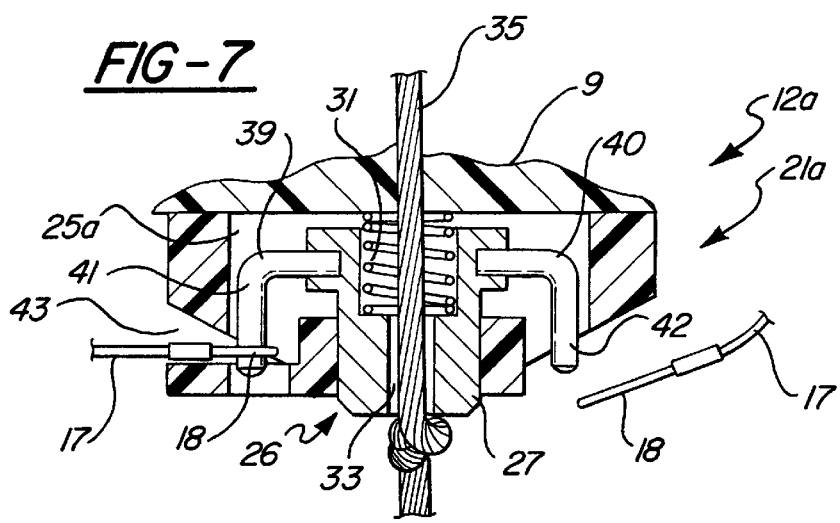

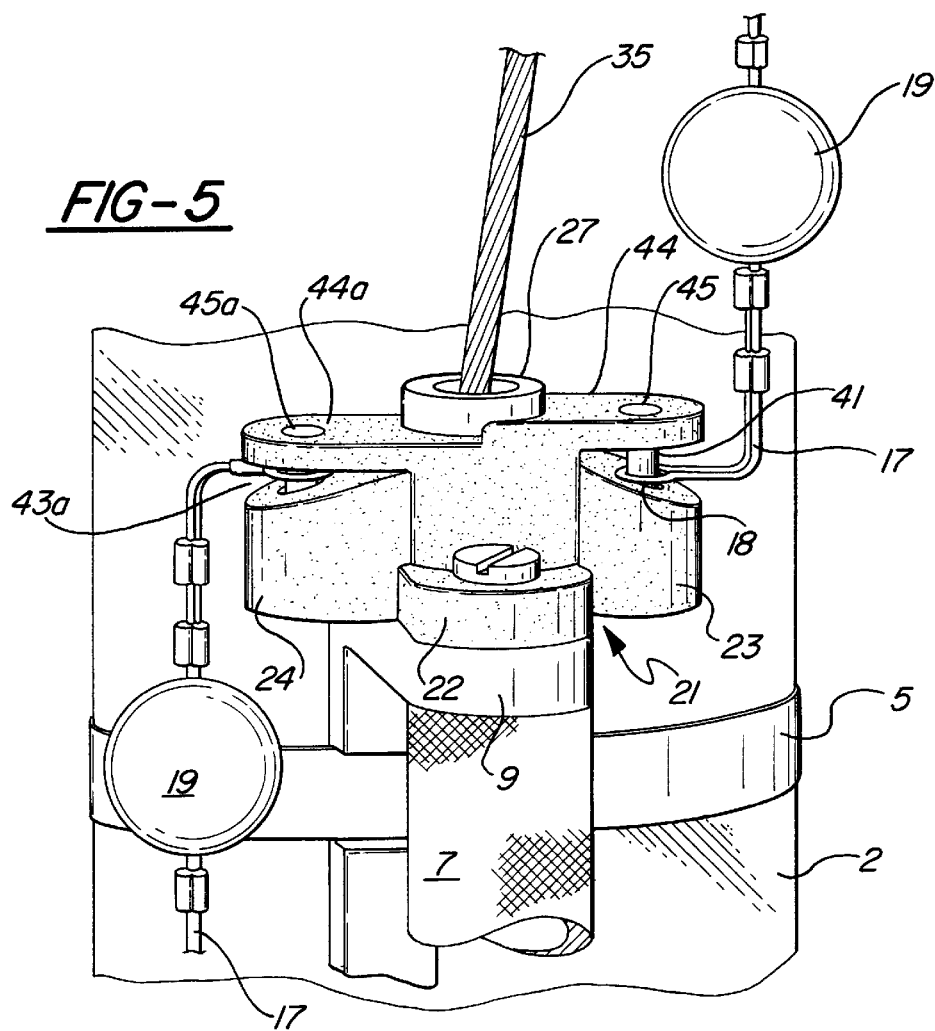
FIG-5
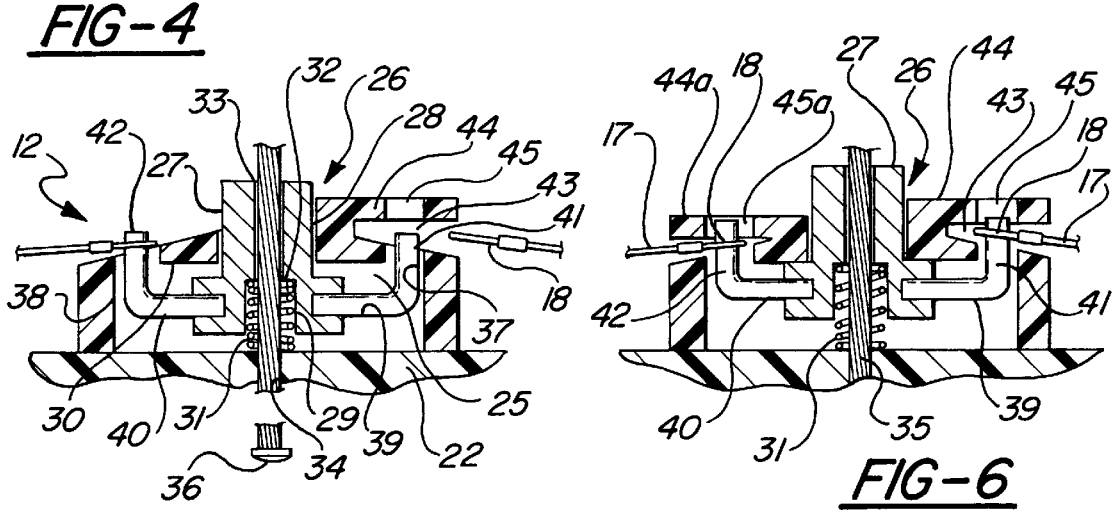
FIG-4
FIG-6

UNDERWATER SAMPLING APPARATUS

BACKGROUND OF THE INVENTION

For some liminological and oceanographic studies it is important that underwater samples be taken at selected depths and that such samples be protected against dilution or modification due to leakage of the sampler during retrieval of the latter. One type of sampler used for this purpose comprises a hollow tube, usually open at both ends, and having end closures or stoppers which are adapted to be moved from open positions to closed, sealing positions in response to the dropping of a weighted messenger along the tether line or cable which supports the sampler. The stoppers are latched in their open positions by a releasable latch mechanism which has a release assembly that is tripped by compressive force generated by the weighted messenger to enable the stoppers to move to their closed positions. Such a latch mechanism is disclosed in U.S. Pat. No. 3,949,497, granted Apr. 13, 1976.

Some of the water samplers comprise hollow tubes which are adapted to be suspended substantially horizontally in the water, whereas others comprise hollow tubes that are adapted to be suspended vertically. In either case the closures at the ends of the tube are adapted to be moved from open to closed position when desired and at whatever level the samplers are located.

Effecting closing movement of the closures at opposite ends of a vertically suspended tube presents a special problem. This primarily is due to the fact that the latch mechanism associated with the uppermost closure must be capable of overcoming an upward force exerted by the cable which retains the uppermost closure in its open position. To accomplish this objective vertical water samplers have been fitted with extremely complex latch release mechanisms.

A principal object of the invention is to provide a simple, inexpensive, easily operable, releasable latch mechanism for latching closures at opposite ends of a vertically oriented water sampler in their open position, but which assures release of the latch mechanism when desired so as to enable the closures to move from their open position to their closed position.

SUMMARY OF THE INVENTION

A water sampler constructed in accordance with the invention has a tubular body open at both ends and closures or stoppers which normally close and seal the ends of the tube, but which may be latched in positions in which the ends are open. An elastic member extends through the tube and connects the two closures, and such elastic member is operable to exert sufficient force on both of the closures to move them into sealing relation with the respective ends of the tubular body.

A handle is secured to the tubular body to facilitate handling of the sampler and such handle is provided with a latching mechanism which is operable releasably to latch the closures in their open positions. The latching mechanism comprises a body having opposite ends at least one of which has a slot extending inward of the body so as to form a recess having spaced apart walls. Slideably accommodated in the body of the latch mechanism is an operating member that is connected to two oppositely extending retainers which are movable in such directions as to enable one of them to pass into and out of the recess. The retainers may be connected to anchor members which are secured to the closures so that, in one position of the retainers, the closures releasably may be latched in their open positions.

In one embodiment of the invention the operating member is displaceable by a weighted messenger in such direction as to enable the anchor members to be released from the retainers, whereupon the closures are moved by the elastic connecting member to their closed position.

In another embodiment of the invention a tether line is coupled to the operating member and is operable to displace the latter in such direction that the retainers release the anchor members, whereupon the closures move to the closed position.

THE DRAWINGS

Three embodiments of the invention are illustrated in the accompanying drawings, wherein:

FIG. 2 is a fragmentary view, on an enlarged scale, of the latch embodiment shown in FIG. 1;

FIG. 4 is a sectional view illustrating the latching mechanism of the first embodiment in an intermediate position;

FIG. 5 is a view similar to FIG. 2 but illustrating a modified embodiment of the invention;

FIG. 6 is a sectional view similar to FIG. 5, but showing the second latch embodiment in latching position; and FIG. 7 is a sectional view similar to FIG. 5 but illustrating a third latch embodiment.

THE PREFERRED EMBODIMENTS

Figure 1:
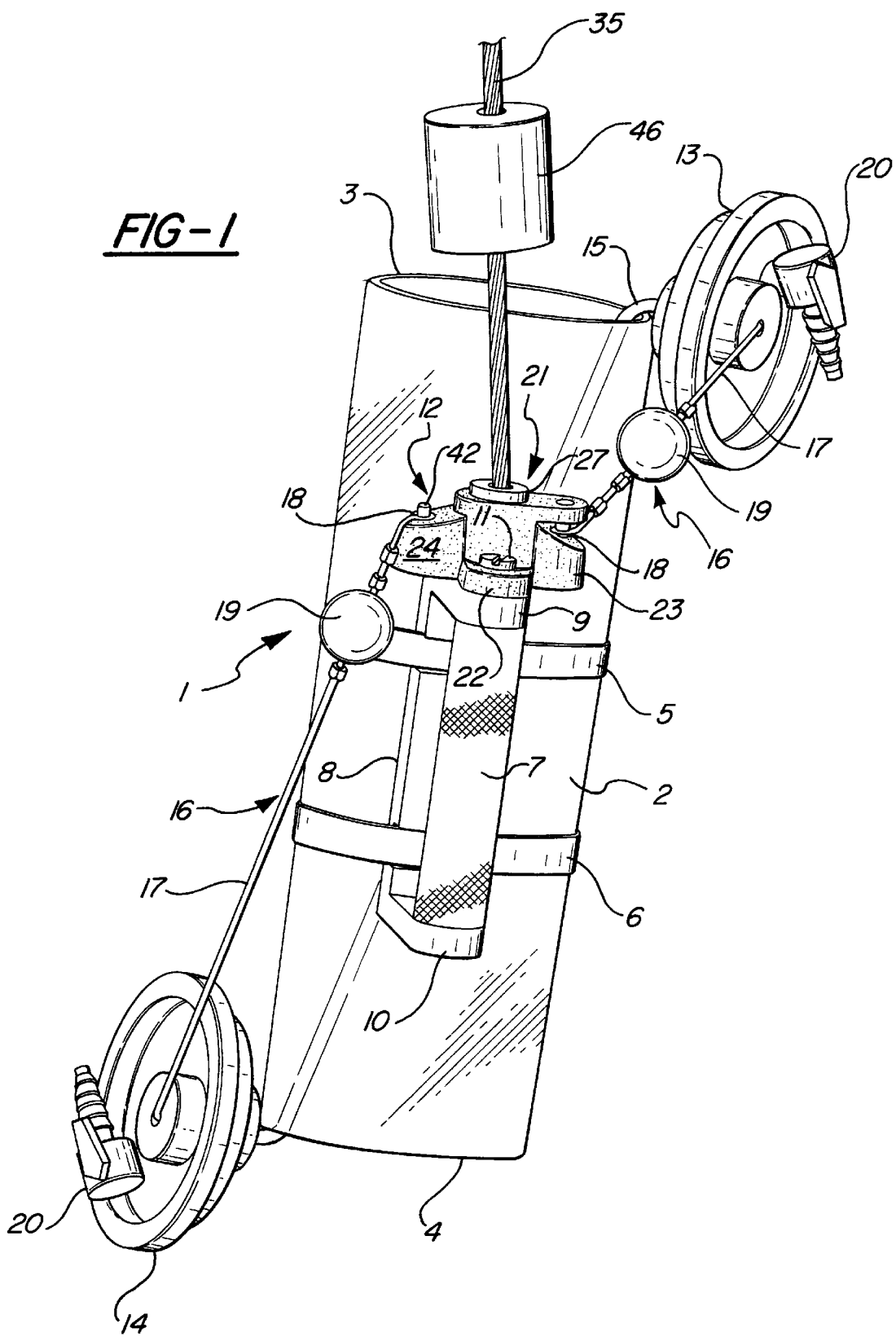
FIG. 1 is an elevational view of one embodiment showing the closures in their open position.

A water sampler adapted for use with all embodiments of the latch mechanism is designated generally by the reference character 1 and comprises a hollow, preferably transparent tube 2 open at its opposite ends 3 and 4. Secured to the exterior of the tube 2 by clamp bands 5 and 6 is a handle 7 having a base 8 which underlies the bands and terminates at its opposite ends in flanges 9 and 10. Seated on the flange 9 and secured thereto by a screw 11 or the like is a latch mechanism 12 which will be described in more detail subsequently.

At one end of the tube 2 is a closure or stopper 13 of conventional construction. A similar stopper 14 is provided for the opposite end of the sampler. Secured to the stopper 13 is one end of an elastic connecting member, the opposite end of which is secured to the closure 14. The elastic member 15 is of such length and of such strength that it normally is capable of moving the closures 13 and 14 quickly and forcibly from their open positions shown in FIG. 1 to their closed positions shown in FIG. 3, as is conventional.

Secured to the closure 13 is one end of an anchor member 16 comprising an inelastic, flexible cable 17 which terminates at its other end in an arcuate or annular fitting 18. Fixed to the cable 17 between its ends is an enlargement 19 which facilitates manual manipulation of the closure 13. Fitted to the closure 13 is a valve 20 which in one position prevents the passage of water through the closure 13, but which in another position enables the sampler to be drained.

The closure 14 is provided with anchor apparatus 16 corresponding to that associated with the closure 13. Accordingly, the same reference characters are applied to the anchor device associated with the closure 14. The only difference between the two anchor devices is that the cable 17 associated with the closure 14 is longer than the other cable 17 because the latch mechanism 12 is farther from the tube end 4 than it is from the tube end 3.

The latch mechanism 12 comprises a body 21 having a pedestal 22 which seats on the flange 9. The body 21 has two opposite ends 23 and 24 between which is a chamber 25 (FIG. 4). Accommodated in the chamber 25 is an operating member 26 having a hollow stem 27 which extends through an opening 28 formed in the body 21 so as normally to project above the upper level of the body (FIG. 2). The operating member 26 also has an enlargement 29 that is accommodated in the chamber 25 and normally is biased to a position in which it bears against the upper wall 30 of the chamber by a compression spring 31 which reacts between the base 22 and a blind bore 32 in the operating member 26. The operating member 26 has a tubular passage 33 therethrough in register with a similar passage 34 in the base 22 and a corresponding passage in the flange 9 through which extends a hoist or tether line 35 by means of which the sampler 1 may be lowered to and raised from a body of water (not shown). The line 35 has an enlargement 36 at its lower end to prevent its being pulled from the sampler.

In communication with the chamber 25 is a pair of spaced apart openings 37 and 38. Extending laterally from the operating member 26 and coupled thereto is a pair of L-shaped retainers 39 and 40, the retainer 39 having an upstanding leg 41 which extends through the opening 37 and the retainer 40 having an upstanding leg 42 which extends upwardly through the opening 38.

At the end 23 of the body 21 is a slot or notch which forms a recess 43 having upper and lower walls that converge toward the center of the body. The notch also forms a wall or flange 44 overlying the recess and having an opening 45 in register with the opening 37.

To condition the apparatus thus far described for operation, and before the sampler is lowered into the water, the closure 14 may be moved off its seat at the end 4 of the tube 2 and the free end of the anchor cable 17 moved toward the latch mechanism 12 to enable the anchor fitting 18 to be secured to the retainer 42. See FIG. 2. The operating member 26 then manually may be displaced downwardly so as to remove the free end of the retainer leg 41 from the opening 45 a distance sufficient to enable the anchor fitting 18 of the other cable 17 to be slipped over the free end of the leg 41. See FIG. 4. Although the retainer legs 41 and 42 are of equal length, the construction is such that the operating member 26 may be displaced downwardly a distance sufficient to provide clearance between the retainer leg 41 and the flange 43 sufficient to pass the anchor fitting 18 while the other anchor fitting 18 remains secured to the retainer leg 42.

Once the fittings at the free ends of the two anchor cables are secured to their respective retainers, the operating member 26 may be released whereupon it will be moved upwardly by the spring 31 from the position shown in FIG. 4 to provide greater security for the attachment of the anchor cables to the retainers 41 and 42.

Following securing of the closures 13 and 14 in their open positions, the sampler may be lowered by the hoist cable 35 to a predetermined depth in a body of water. At that time an actuator comprising a weighted messenger 46 may be permitted to slide down the hoist line 35 until it strikes the upwardly projecting tubular part 27 of the operating member 26, thereby displacing the operating member downwardly a distance sufficient to enable the anchor fittings 18 to be released from the retainer legs 41 and 42. The elastic member 15 then will cause the closures 13 and 14 to move rapidly to their closed positions, thereby sealing the interior of the tubular body 2. The sampler then may be raised by the hoist line 35 to enable the sample contained in the sampler to be discharged therefrom for analysis.

The embodiment shown in FIGS. 5 and 6 correspond in many respects to the embodiment just described. The principal difference between the two embodiments is that the embodiment of FIGS. 5 and 6 has a slot at the end 24 of the latch mechanism body 21 which forms a recess 43a corresponding to the recess 43 and providing a wall 44a corresponding to the wall 44. The wall 44a has an opening 45a therein through which the retainer leg 42 may project. As is shown clearly in FIGS. 5 and 6, the wall 44a is at a level somewhat lower than that of the wall 44 as a consequence of which the height of the recess 43 is greater than that of the other recess. However, the retainer legs 41 and 42 are of equal length, thereby enabling the anchor fittings 18 to be secured to their respective retainers in succession. The wall 44a provides greater security for inadvertent disengagement of the anchor cable 17 from the retainer 42 due to rough handling of the sampler.

Figure 3:
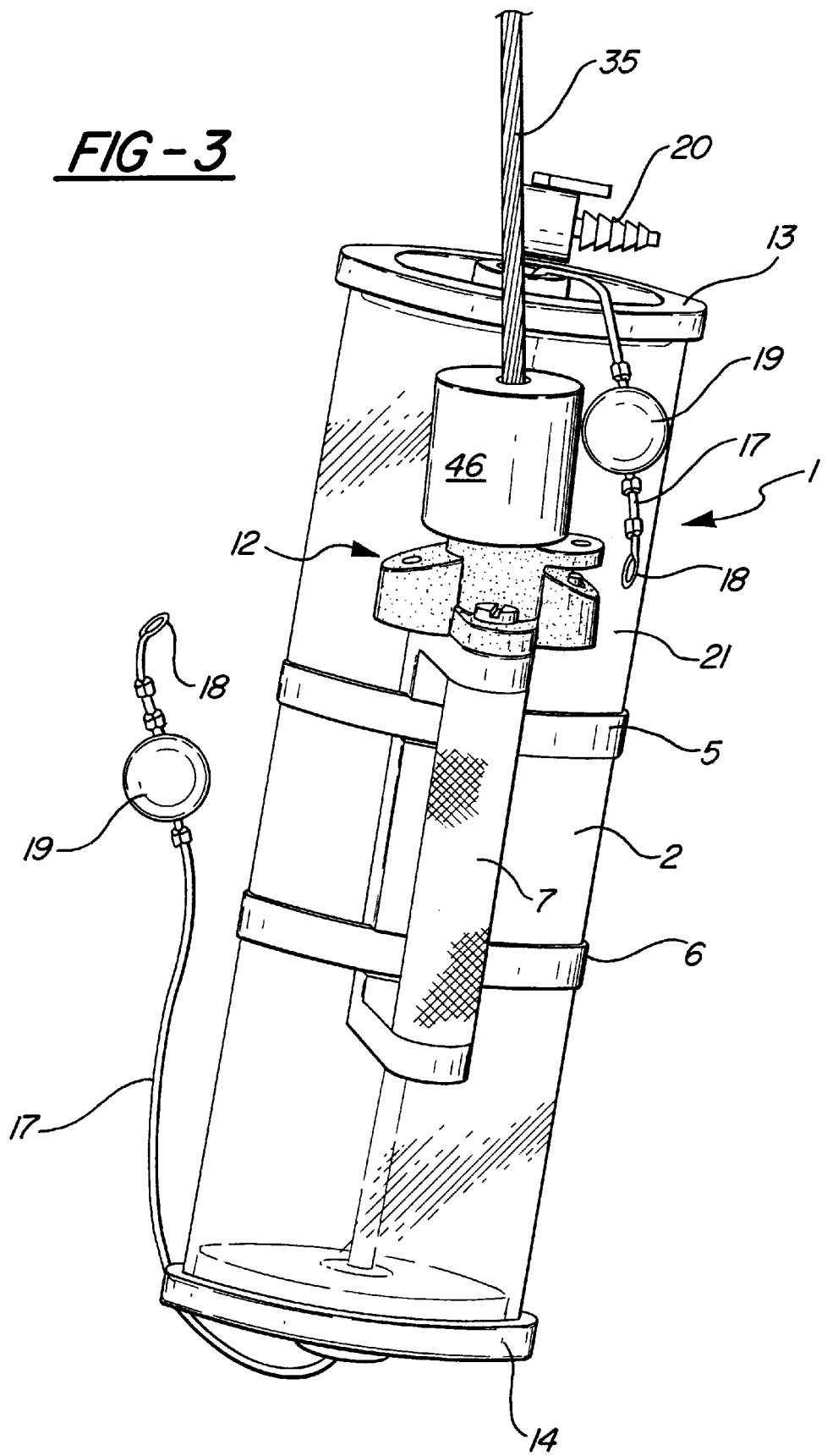
FIG. 3 is a view similar to FIG. 1 but showing the closures in their closed position.

The embodiment of the invention shown in FIG. 7 corresponds substantially to that disclosed in FIGS. 1–3 with the exception the latch mechanism 12a is housed within a body 21a which is upside down compared to the body 21 of the earlier embodiment. In the FIG. 7 embodiment, the body 21a is secured beneath the handle flange 9 and has a chamber 25a within which is the operating member 26 and the retainer members 39 and 40, but in this case the fingers 41 and 42 extend downwardly. In all other respects the latch mechanism 12a corresponds to the mechanism 12. However, the hoist line 25 is knotted or otherwise enlarged so as to be incapable of passing upwardly through the bore 33 in the operating member 26.

In the operation of the mechanism 12a, the operating member 26 may be displaced upwardly so as to enable the anchor fittings 16 to be assembled with their respective retainer members 39, 40. The spring 31 biases the operating member to a lowered, projected position so as to maintain the closures at the opposite ends of the sampler body in their open positions. Following lowering of the sampler to the predetermined level, a sharp, upward tug on the hoist line 35 will overcome the bias of the spring 31 and move the operating member 26 in an upward direction, thereby enabling the anchor cables 17 to be disengaged from the retainers 39 and 40, following which the closures at the opposite ends of the sampler body will be moved to their closed positions. In this embodiment the hoist line 35 not only performs the function of raising, lowering, and suspending the sampler, but it also constitutes the actuating means for the operating member 26. The force exerted by the line 35 must have a threshold value greater than the force exerted by the spring 31.

The disclosed embodiments are representative of presently preferred forms of the invention, but are intended to be illustrative rather than definitive thereof. The invention is defined in the claims.

We claim:

1. In underwater sampling apparatus having a tubular container open at its opposite ends, a first closure member for closing one end of said container and a second closure member for closing the other end of said container, an elastic connecting member interconnecting said closure members and biasing said closure members toward their closed position, a latch mechanism, anchor means reacting between said latch mechanism and each of said closure members for releasably maintaining said closure members in their open positions, and operating means operable to release said latch mechanism, the improvement wherein said latch mechanism comprises a body having opposite ends; a first retainer for connection to one of said anchor means and slideably accommodated in an opening at one end of said body; a second retainer for connection to the other of said anchor means and slideably accommodated in a second opening at the opposite end of said body; means coupling said first and second retainers for conjoint sliding movements thereof, at least one of said ends of said body having a recess therein into and out of which the retainer at said one end of said body and one of said anchor means may pass, said recess being of such dimension as to accommodate both the retainer at said one end of said body and said one of said anchor means for latching one of said closure members in its open position; and actuating means cooperable with said operating means for disengaging said retainers and said anchor means, thereby enabling said connecting member to move said closure members to their closed position.

2. Apparatus according to claim 1 wherein the other end of said body has a recess therein corresponding substantially to the recess at said one end of said body.

3. Apparatus according to claim 2 wherein one of said recesses has a height greater than that of the other of said recesses.

4. Apparatus according to claim 1 wherein said operating means comprises an operating member slideably accommodated in said body for movements in opposite directions, and said actuating means is operable to effect movement of said operating member in a direction to effect release of said anchor means and said retainers.

5. Apparatus according to claim 4 wherein said actuating means comprises a messenger engageable with said operating member.

6. Apparatus according to claim 4 wherein said actuating means comprises a line coupled to said operating member and operable to displace said operating member in response to the application of tensile force on said line in excess of a predetermined threshold value.

7. A latch mechanism adapted for use with a water sampler having a tube open at least at one end, a closure movable between first and second positions in which said one end is open and closed, respectively, elastic means for moving said closure from said first position to said second position, and an anchor member connecting said closure to said tube, said latch mechanism comprising a body having opposite ends, said body having a recess at least at one end thereof; a retainer slideably accommodated in said body adjacent said one end for movements in opposite directions into and out of said recess, said recess being of such dimension as to accommodate said retainer and a portion of said anchor member; and an operating member slideably accommodated in said body and coupled to said retainer for moving the latter in a direction out of said recess in response to sliding movement in one direction of said operating member.

8. The latch mechanism according to claim 7 wherein said anchor member comprises an arcuate part and said retainer comprises a finger of such dimension as to be embraced by said actuate part.

9. The latch mechanism according to claim 7 including actuating means coupled to said operating member and operable to move said operating member in said direction.

10. The latch mechanism according to claim 9 wherein said actuator means comprises a messenger engageable with said operating member.

11. The latch mechanism according to claim 9 wherein said actuating means comprises a line coupled to said operating member for moving the latter in said direction in response to the application on said line of tensile force in excess of a predetermined value.

12. The latch mechanism according to claim 7 including a second recess at the opposite end of said body and a second retainer slideably mounted adjacent said opposite end of said body for movements in opposite directions into and out of said second recess, said second recess also being of such dimension as to accommodate said second retainer and a portion of said anchor member.

13. The latch mechanism according to claim 12 wherein said operating member also is coupled to said second retainer for moving both of said retainers simultaneously.

14. The latch mechanism according to claim 12 wherein each of said recesses has spaced apart walls, the spacing between said wales of one of said recesses being greater than the spacing between said walls of the other of said recesses.

15. The latch mechanism according to claim 14 where each of said retainers is of uniform length.

16. A latch mechanism comprising a body having opposite ends, at least one of said ends having a slot therein forming a recess having two confronting, spaced apart walls; an opening in communication with said recess; a retainer slideably accommodated in said opening for movements into and out of said recess; an operating member slideably mounted in said body and connected to said retainer to effect said movements in response to corresponding movements of said operating member; biasing means acting on said operating member and yieldably biasing said operating member and said retainer in a direction inward of said recess; and actuating means coupled to said operating member and operable to overcome said biasing means and move said operating member and said retainer in a direction outward of said recess.

17. The latch mechanism according to claim 16 wherein said body has a second slot in its other end forming a second recess having two confronting spaced apart walls, a second opening in said body in communication with said second recess, and a second retainer slideably accommodated in said second opening for movements in opposite directions inward and outward of said second recess, said second retainer being connected to said operating member for conjoint movements therewith.

18. The latch mechanism according to claim 17 wherein the space between the walls of one of said recesses is greater than the space between the walls of the other of said recesses.

19. The latch mechanism according to claim 18 wherein said retainers are uniform in length.

20. The latch mechanism according to claim 16 wherein the walls of said recess converge in a direction inward of said body.

* * * * *

UNITED STATES PATENT AND TRADEMARK OFFICE
CERTIFICATE OF CORRECTION

PATENT NO. : 6,006,613
DATED : December 28, 1999
INVENTOR(S) : Michael L. Dickinson et al It is certified that error appears in the above-identified patent and that said Letters Patent is hereby corrected as shown below:

Column 1, after the title insert the following paragraph:

-- This invention relates to underwater sampling apparatus having a normally open container adapted to be lowered to a selected depth in a body of water following which the conatiner may be closed to entrap in the container a sample of water at the selected level. --

Column 4, line 36, change "16" to -- 18 --.

Column 6, line 22, change "wales" to -- walls --.
On the title page, item [75]:
Change Stacy K. Hilaski residence from "Stanford" to -- Sanford --.

Signed and Sealed this

Eighth Day of August, 2000

Attest:

Attesting Officer

Q. TODD DICKINSON

Director of Patents and Trademarks